United States Patent
McLaughlin et al.

(10) Patent No.: US 10,928,243 B2
(45) Date of Patent: Feb. 23, 2021

(54) VIBRATION MONITOR

(71) Applicant: REACTEC LIMITED, Edinburgh Lothian (GB)

(72) Inventors: Jacqueline McLaughlin, Edinburgh (GB); Mark Paul Buckingham, Edinburgh (GB)

(73) Assignee: REACTEC LIMITED, Edinburgh (GB)

( * ) Notice: Subject to any disclaimer, the term of this patent is extended or adjusted under 35 U.S.C. 154(b) by 342 days.

(21) Appl. No.: 15/756,032

(22) PCT Filed: Sep. 5, 2016

(86) PCT No.: PCT/GB2016/052723
§ 371 (c)(1),
(2) Date: Feb. 27, 2018

(87) PCT Pub. No.: WO2017/037476
PCT Pub. Date: Mar. 9, 2017

(65) Prior Publication Data
US 2019/0025114 A1   Jan. 24, 2019

(30) Foreign Application Priority Data
Sep. 3, 2015   (GB) ..................................... 1515580

(51) Int. Cl.
*G01H 1/00* (2006.01)
*A61B 5/00* (2006.01)
(52) U.S. Cl.
CPC ................ *G01H 1/00* (2013.01); *A61B 5/681* (2013.01)
(58) Field of Classification Search
CPC .......... G01H 1/00; G01H 13/00; A61B 5/681; A61B 5/6802; A61B 5/6801; A61B 5/68; A61B 5/6825
(Continued)

(56) References Cited

U.S. PATENT DOCUMENTS 6,490,929 B1 * 12/2002 Russell ..................... G01H 1/00
                                                                  340/683
10,631,130 B2 * 4/2020 Esenwein ............. H04W 4/029
(Continued)

FOREIGN PATENT DOCUMENTS

DE   102007010800   9/2008
DE   102012021838   5/2014
(Continued)

OTHER PUBLICATIONS

International Search Report of Counterpart PCT International Application No. PCT/GB2016/052723.
(Continued)

*Primary Examiner* — Lisa M Caputo
*Assistant Examiner* — Rose M Miller
(74) *Attorney, Agent, or Firm* — Liu & Liu

(57) ABSTRACT

The present invention relates to a vibration monitor (30) which is configured to be worn by an operator during use of a power tool. The vibration monitor comprises a vibration sensor (36) which is operative to sense vibration sustained by the operator when the vibration monitor (30) is worn by the operator. The vibration monitor (30) further comprises a processor (32) configured to receive sensed vibration data from the vibration sensor (36) and to transform received vibration data whereby the transformed data is more representative than the received vibration data of vibration at a location on a power tool or a workpiece with which the operator is in contact during use of the power tool.

21 Claims, 7 Drawing Sheets

(58) Field of Classification Search
USPC .......................................... 73/658, 587, 579
See application file for complete search history.

(56) References Cited

U.S. PATENT DOCUMENTS

| | | | |
|---|---|---|---|
| 2007/0049836 A1 | 3/2007 | Chen | |
| 2009/0040061 A1* | 2/2009 | Golunski | G07C 3/08 340/683 |
| 2009/0140154 A1* | 6/2009 | Roth | B25F 5/00 250/370.07 |
| 2009/0188323 A1 | 7/2009 | Lueschow | |
| 2009/0192723 A1* | 7/2009 | Jonsson | G01H 3/14 702/19 |
| 2010/0174502 A1 | 7/2010 | Thompson et al. | |
| 2014/0176422 A1 | 6/2014 | Brumback et al. | |

FOREIGN PATENT DOCUMENTS

| | | |
|---|---|---|
| EP | 1586875 | 10/2005 |
| EP | 1752747 | 2/2007 |
| EP | 1973077 | 9/2008 |
| EP | 2083252 | 7/2009 |
| EP | 2273244 | 1/2011 |
| EP | 3064911 | 9/2016 |
| GB | 2299168 | 9/1996 |
| GB | 2411472 | 8/2005 |
| GB | 2438219 | 11/2007 |
| GB | 2472674 | 2/2011 |
| GB | 2495559 | 4/2013 |
| WO | 2010/041059 | 4/2010 |
| WO | 2013083943 | 6/2013 |
| WO | 2014072044 | 5/2014 |

OTHER PUBLICATIONS

Bovenzi, "A Longitudinal Study of Vibration White Finger, Cold Response of Digital Arteries, and Measures of Daily Vibration Exposure", International Archives of Occupational and Environmental Health, Springer, Berlin, Germany, vol. 83, No. 3, Sep. 4, 2009, pp. 259-272.

* cited by examiner

VIBRATION MONITOR

FIELD OF THE INVENTION

The present invention relates to a vibration monitor configured in particular but not exclusively to monitor hand arm vibration sustained during use of the like of power tools. The present invention also relates to a vibration monitoring arrangement comprising such a vibration monitor. The present invention further relates to a method of monitoring vibration sustained by an operator.

BACKGROUND ART

Hand held and hand guided powers tools often transmit vibration to the hands and arms of a power tool operator. It is known that such transmitted vibration, which is usually termed Hand Arm Vibration (HAV), can lead to painful and disabling disease, such as white finger, as a consequence of long term exposure.

Vibration monitors for monitoring vibration sustained during use of power tools are known. GB 2299168 discloses a vibration monitor which is worn on the wrist of an operator during use of vibrating apparatus. The vibration monitor of GB 2299168 senses vibration and determines the duration of vibration that exceeds a threshold level. WO 2007/072068 discloses apparatus for monitoring vibration of a hand held power tool. The apparatus of WO 2007/072068 comprises a mount and a monitoring unit. The mount is attached to the power tool and the monitoring unit, which is personal to an operator, is releasably attached to the mount when the operator is using the tool. The mount stores an identification code and a vibration dosage rate for the power tool to which it is attached. When the monitoring unit is attached to the mount the identification code and the vibration dosage rate are conveyed to the monitoring unit. The monitoring unit is operative to sense vibration and to determine the duration of vibration that exceeds a vibration threshold level. The monitoring unit is further operative to multiply the determined duration by the vibration dosage rate to provide a vibration exposure level for the operator.

The present inventors have recognised that the above described approaches have shortcomings. The present invention has been devised in light of the inventors' appreciation of such shortcomings. It is therefore an object for the present invention to provide an improved vibration monitor configured to monitor hand arm vibration sustained during use of a power tool. It is a further object for the present invention to provide an improved method of monitoring hand arm vibration sustained during use of a power tool.

Statement of Invention

According to a first aspect of the present invention there is provided a vibration monitor which is configured to be worn by an operator during use of a power tool, the vibration monitor comprising:
  a vibration sensor operative to sense vibration sustained by the operator when the vibration monitor is worn by the operator; and
  a processor configured to receive sensed vibration data from the vibration sensor and to transform received vibration data whereby the transformed data is more representative than the received vibration data of vibration at a location on a power tool or a workpiece with which the operator is in contact during use of the power tool.

The vibration monitor according to the present invention is configured to be worn by an operator. The vibration monitor comprises a vibration sensor operative to sense vibration sustained by the operator and more specifically during use of a power tool, such as an electrically powered tool or a pneumatically powered tool. The vibration monitor may be configured such that it is worn by the operator at a location spaced apart from the operator's fingers, such as on a wrist of the operator. The vibration sensor may thus be at the spaced apart location. The vibration monitor also comprises a processor which is configured to receive sensed vibration data from the vibration sensor and to transform the received vibration data. The transformed data is more representative than the received vibration data of vibration at a location on a power tool or a workpiece with which the operator is in contact during use of the power tool. Vibration sensed at a location other than the location on the power tool or the workpiece with which the operator is in contact during use of the power tool, such as the wrist, differs from vibration at the location on the power tool or the workpiece with which the operator is in contact. The vibration sensed at a location other than the location on the power tool or the workpiece with which the operator is in contact may, for example, differ in respect of being damped or exhibiting frequency dependent behaviour such as resonance. Transforming the received vibration data therefore provides transformed data which is more representative of vibration at the location on the power tool or the workpiece with which the operator is in contact during use of the power tool.

The vibration monitor may comprise a data store, such as data memory comprised in the processor, which stores a transformation which is operative to transform vibration data received from the vibration sensor.

The body of the operator between a point of contact with a power tool or a workpiece and the location of the vibration sensor may attenuate vibration sustained at the point of contact. The transformation may be configured to amplify the received vibration data to thereby address the attenuation. More specifically the transformation may be configured to amplify the received vibration data in a predetermined range of frequencies, such as between 6 Hz and 16 Hz. The transformation may be configured to substantially neither amplify nor attenuate the received vibration data above the predetermined range of frequencies, such as above 16 Hz. The transformation may be configured to attenuate the received vibration data below the predetermined range of frequencies, such as below 6 Hz. More specifically the transformation may be configured to substantially completely attenuate the received vibration data below the predetermined range of frequencies and perhaps in a further range of frequencies below the predetermined range of frequencies.

The transformation may be configured to attenuate the received vibration data in a low frequency range, amplify the received vibration data in a medium frequency range and to neither substantially amplify nor substantially attenuate the received vibration data in a high frequency range.

The transformation may be configured to amplify received vibration data of a frequency of at least 2 Hz, 4 Hz, 6 Hz or 8 Hz. The transformation may be configured to amplify received vibration data of a frequency of no more than 20 Hz, 18 Hz, 16 Hz or 14 Hz.

The transformation may be configured to amplify received vibration data by a factor of at least 1.1, 1.2, 1.3, 1.4, 1.5, 1.6, 1.7, 1.8 or 1.9. The transformation may be configured to amplify received vibration data by a factor of no more than 2.0, 1.9, 1.8, 1.7, 1.6, 1.5, 1.4, 1.3 or 1.2.

The body of the operator between a point of contact with a power tool or a workpiece and the location of the vibration sensor may amplify vibration at the point of contact. Attenuation and amplification may take place in respect of different frequency bands. Alternatively or in addition, the transformation may be configured to attenuate the received vibration data to thereby address the amplification.

The resonant frequency for the whole body of a person is normally in the range of 2 Hz to 4 Hz with the actual frequency value depending on the anatomy of the person in question in respect of stiffness and mass. Different parts of the body resonate at different frequencies. For example the wrist has a resonant frequency in the range of 12 Hz to 16 Hz with the actual value depending again on the anatomy of the person in question. Vibration at a point of contact with a power tool or a workpiece may cause resonance whereby vibration of the power tool at and around the resonant frequency may be more damaging to the operator. The transformation may be configured to take account of resonance of the body of the operator by, for example, attenuation of the received vibration data as described above. Alternatively the transformation may be configured for a resonant frequency of an average operator. Configuration of the transformation may be accomplished during a calibration stage as described below.

Different power tools exhibit different patterns of vibration. The vibrations of one power tool may be of lower amplitude than the vibrations of another power tool. Furthermore the difference between amplitudes of vibrations for different power tools may vary across a frequency spectrum of interest. The transformation may therefore be configured for one of plural classes of power tool. For example one class of power tool may be constituted by pneumatic tools which exhibit higher amplitude vibration at low frequencies and another class of power tool may be constituted by electric drills which exhibit higher amplitude vibration at high frequencies. The transformation may be configured accordingly. Configuration of the transformation may be accomplished during a calibration stage as described below.

In another embodiment, the transformation may not be configured for a particular power tool or for one of plural classes of power tool. The transformation may thus be operative irrespective of the vibration characteristics of the power tool with which the vibration monitor is used. The same transformation may be used with different power tools. In contrast with known vibration monitors, the vibration monitor of the present invention may therefore be operative without knowledge of the vibration characteristics of the power tool. Furthermore the vibration monitor of the present invention may be used by a person who is in contact with a workpiece, such as by way of gripping the workpiece, whereby the person is not in direct contact with the power tool which is causing vibration of the workpiece.

The data store may store plural different transformations. Each transformation may be for a different one of: class of power tool; and particular power tool. In addition, the transformation may take account of an operator or an average operator as described above. The vibration monitor may be configured for selection of one of the plural different transformations. More specifically the vibration monitor may be configured for user operation, such as by way of a user actuable control, for selection of one of the plural different transformations. Alternatively or in addition, the vibration monitor may be configured for selection of one of the plural different transformations in dependence on receipt of power tool data, such as power tool data received from the tool arrangement as described below. The selection may be in dependence on power tool identification data comprised in the power tool data, the power tool identification data identifying one of a class of power tool and a particular power tool. The vibration monitor may thus be configured for use with a class of power tool or a particular power tool.

The processor may be configured to analyse a frequency spectrum of vibration data. More specifically the processor may be configured to determine a dominant frequency or plural dominant frequencies. The processor may be further configured to determine how vibration data is to be filtered in dependence on the determination of at least one dominant frequency. For example, one of a low pass filter, band pass filter and high pass filter may be applied to the vibration data depending on the determination of at least one dominant frequency.

The vibration monitor may comprise an analogue to digital converter which is operative to sample an output from the vibration sensor. The analogue to digital converter may be operative to sample an output from the vibration sensor at a rate of at least 1 kHz, 1.2 kHz, 1.4 kHz, 1.6 kHz, 1.8 kHz or 2 kHz.

The processor may be configured to transform time domain vibration data from the vibration sensor to frequency domain vibration data. The processor may be configured to perform a Fourier transform and more specifically an overlapping windowed Fourier transform, such as Welch's method. The processor may be operative to form plural frequency bands, the frequency bands being between 500 and 1300, between 700 and 1100 or between 800 and 1000. For example, there may be 896 frequency bands. The lower limit of the frequency bands may be 0 Hz, 1 Hz, 2 Hz, 3 Hz, 4 Hz, 5 Hz or 6 Hz. The upper limit of the frequency bands may be 150 Hz, 160 Hz, 170 Hz, 180 Hz, 190 Hz, 200 Hz, 210 Hz, 220 Hz, 230 Hz, 240 Hz, 250 Hz, 260 Hz, 270 Hz, 280 Hz, 290 Hz, 300 Hz, 310 Hz, 320 Hz or 325 Hz. A Power Spectral Density (PSD) may be determined in dependence on the frequency domain data. Furthermore an energy value may be determined by integration over a predetermined interval. For example, the energy value may be determined in respect of the frequency range 0 Hz to 325 Hz.

The processor may be configured to determine a root mean square value of vibration data and more specifically a root mean square value of frequency domain vibration data. Root mean square values may be determined after transformation to provide more representative data as described above. Furthermore the processor may be configured to sum root mean square values and more specifically sum root mean square values of frequency domain vibration data. The summing may be after transformation to provide more representative data as described above. The processor may thus be operative to provide a single value that represents the amplitude of the sensed vibration. The processor may be operative to determine the root mean square value in accordance with:

$$a_{hw} = \sqrt{\sum_i (W_{hi} a_{hi})^2}$$

where $a_{hw}$ is the root mean square acceleration, $W_{hi}$ is a weighting factor for the i th one-third-octave band applied by way of the transformation and $a_{hi}$ is the acceleration measured in the i th one-third-octave band in metres per second squared.

The processor may be configured to weight vibration data and more specifically to weight frequency domain vibration data. The frequency domain vibration data may be weighted in accordance with ISO 5349-1. The weighting may be in respect of frequencies below 6 Hz. The weighting may be comprised in the transformation. The weighting may be before summing as described above.

Where the vibration sensor is a tri-axial vibration sensor, the processor may be further configured to combine vibration data in three axes received from the vibration sensor. More specifically the processor may be configured to sum vibration data in each of the three axes. The processor may be configured to sum the square of vibration data in each of the three axes. More specifically the processor may be configured to determine the square root of the sum of the square of vibration data in each of the three axes. The processor may be configured to combine vibration data in three axes in accordance with:

$$a_{hv} = \sqrt{a_{hwx}^2 + a_{hwy}^2 + a_{hwy}^2}$$

where $a_{hv}$ is the combined value for the three axes and $a_{hwx}$, $a_{hwy}$ and $a_{hwy}$ are the root mean square values for the x, y and z axes respectively as determined in accordance with the equation above. The value obtained may be a vibration level value.

Alternatively or in addition and where the vibration sensor is a tri-axial vibration sensor, the processor may be further configured to combine vibration data in three axes, x, y and z, in accordance with:

$$a_v(t) = \sqrt{[K_x a_x(t)]^2 + [K_y a_y(t)]^2 + [K_z a_z(t)]^2}$$

where $K_x$, $K_y$ and $K_z$ are weighting factors. Furthermore the processor may be configured to determine a Fourier transform for the combined vibration data.

The processor may be configured to determine a period of exposure of the operator to vibration sensed by the vibration sensor. The processor may comprise a timer which operates in dependence on vibration data received from the vibration sensor. Low amplitude vibration may be of no or little relevance to vibration exposure. For example there may be vibration of low amplitude of a floor on which the operator is standing and which is sustained by way of the legs of the operator. Such vibration may make no or little contribution to hand arm vibration. By way of further example, a power tool may vibrate at an amplitude which is considered to be below a level that contributes to potentially damaging hand arm vibration. The processor may therefore compare an amplitude of vibration data with a threshold amplitude value and start the timer if the amplitude of vibration data exceeds or is at least the same as the threshold amplitude value. The timer may be stopped if the amplitude of vibration data is less than or no more than the threshold amplitude value. The threshold amplitude value may be at least $0.5 \text{ m/s}^2$, $0.6 \text{ m/s}^2$, $0.8 \text{ m/s}^2$, $1.0 \text{ m/s}^2$, $1.2 \text{ m/s}^2$, $1.4 \text{ m/s}^2$, $1.6 \text{ m/s}^2$, $1.8 \text{ m/s}^2$, $2.0 \text{ m/s}^2$, $2.2 \text{ m/s}^2$, $2.4 \text{ m/s}^2$, $2.6 \text{ m/s}^2$, $2.8 \text{ m/s}^2$, $3.0 \text{ m/s}^2$, $3.2 \text{ m/s}^2$, $3.4 \text{ m/s}^2$, $3.6 \text{ m/s}^2$, $3.8 \text{ m/s}^2$ or $4.0 \text{ m/s}^2$.

Certain frequencies of vibration may be of no or little relevance to vibration exposure. For example hand movement, such as hand waving, or the putting down of equipment other than a power tool may give rise to vibration of no relevance to vibration exposure. Such forms of vibration may be distinct from vibration from operation of a power tool. For example, such vibration may be of lower frequency than power tool vibration or may be confined to a relatively narrow band of frequencies. The processor may therefore comprise a filter which is operative to filter vibration data. The filter may comprise at least one of a high pass filter and a notch filter. A high pass filter may, for example, be configured to attenuate low frequency vibration data arising from hand waving or the like and to pass higher frequency vibration data arising from operation of a power tool. A notch filter may, for example, be configured to attenuate frequencies of vibration data within a narrow band arising from an operator putting down equipment other than a power tool and to pass frequencies of vibration data outside the narrow band. The filter may be configured to pass frequencies of at least 1 Hz, 2 Hz, 4 Hz, 6 Hz, 8 Hz, 10 Hz, 12 Hz, 14 Hz, 16 Hz, 18 Hz, 20 Hz, 22 Hz, 24 Hz, 26 Hz or 28 Hz. The filter may be configured to pass frequencies of no more than 2 Hz, 4 Hz, 6 Hz, 8 Hz, 10 Hz, 12 Hz, 14 Hz, 16 Hz, 18 Hz, 20 Hz, 22 Hz, 24 Hz, 26 Hz, 28 Hz or 30 Hz.

At least one of the steps of comparing with a threshold amplitude value and filtering of vibration data may be before a vibration value is determined. Processing of vibration data, such as comparison with a threshold amplitude value and filtering of vibration data, may be in respect of vibration data acquired from the vibration sensor by way of an analogue to digital converter.

The processor may be operative to determine a vibration exposure in dependence on a period of exposure and a vibration level value. The vibration exposure may be determined by multiplying the square of the vibration level value by the period of exposure. Vibration exposure determined in dependence on vibration level value may provide a more useful measure of risk than vibration exposure determined in dependence on a predetermined vibration value as described below. The processor may be operative to record at least one vibration exposure. More specifically plural vibration exposures may be recorded by accumulating the plural vibration exposures determined, for example, during a predetermined time such as a day. A daily vibration exposure may be determined in accordance with ISO 5349-1.

The processor may be configured to determine a vibration exposure in dependence on a period of exposure and a predetermined vibration value. In accordance with the description above, the present vibration exposure may be recorded and more specifically plural vibration exposures may be recorded by accumulating the plural vibration exposures determined, for example, during a predetermined time such as a day. A daily vibration exposure based on the predetermined vibration value may be determined in accordance with ISO 5349-1. The vibration exposure may be determined by multiplying the square of the predetermined vibration value by the period of exposure. The predetermined vibration value may be determined during a calibration phase for a power tool. This is in contrast to the approach of determining a vibration level value as described above which is determined in dependence on vibration sensed by the vibration sensor during use of the vibration monitor. The predetermined vibration value may be stored in the tool arrangement as described below.

The predetermined vibration value for a power tool may be determined in dependence on measurement of vibration of the power tool during a calibration phase. The vibration may be measured by vibration measuring apparatus other than the vibration monitor. The vibration measuring apparatus may be operative to sample vibration of the power tool at a rate and within a bandwidth in accordance with the figures specified above for the vibration monitor. A weighting transformation may be applied to the sampled vibration to attenuate frequency components that are considered not to be harmful. The weighting transformation may comprise a band limiting filter and a weighting filter with the band limiting filter and the weighting filter being cascaded to provide the weighting transformation. The band limiting filter and the weighting filter may have a form as defined in ISO 5349-1.

After application of the weighting transformation, sampled vibration may be subject to determination of root mean square values and combination of vibration data in three axes as described above to provide a tool vibration value. The predetermined vibration value is the thus determined tool vibration value which is then stored for subsequent use during monitoring of vibration.

The vibration monitor may be configured to select at least one of a vibration level value as determined in dependence on sensed vibration and a predetermined vibration value for determination of vibration exposure.

The processor may be operative to determine an operator exposure value in dependence on the transformed vibration data and the energy value. The operator exposure value may further depend on vibration exposure based on a predetermined vibration value. The operator exposure value may further depend on at least one of: period of exposure; and tool type as read from a power tool as power tool identification data or as determined in dependence on at least one dominant frequency in the frequency spectrum of vibration data. The operator exposure value may be formed by summing these factors. More specifically each factor may be multiplied by a constant. The constants may be set during calibration to provide appropriate weighting of the various factors.

The vibration monitor may be configured to be attached and more specifically releasably attached to the operator. The vibration monitor may be configured to be attached to a limb of the operator, for example, to the arm and more specifically to the wrist of the operator. The vibration monitor may have the form of a wrist watch. The vibration monitor may therefore comprise an attachment arrangement, such as a strap or a band, whereby the vibration monitor may be attached to the arm and more specifically the wrist. The attachment arrangement may be configured such that vibration is coupled properly to the vibration monitor and more specifically vibration in a relevant frequency band is coupled to the vibration monitor. The attachment arrangement may be configured such that it is substantially inelastic when the vibration monitor is attached to the operator.

The vibration monitor may comprise a housing. The housing may contain the vibration sensor and the processor. The attachment arrangement may be attached to an exterior of the housing. The housing may be formed at least in part of a substantially rigid material whereby vibration is coupled from the operator to the vibration sensor. The housing may be formed at least in part from a plastics material, such as PC-ABS.

The vibration sensor may comprise a tri-axial vibration sensor. The vibration sensor may comprise an accelerometer.

The processor may comprise a microcontroller. Alternatively or in addition the processor may comprise electronic circuitry further to or instead of a microcontroller, the electronic circuitry being configured to perform processes described herein.

The vibration monitor may comprise a display, such as an LCD display. The LCD display may be supported by the housing. The vibration monitor may be configured to display vibration exposure as determined by the vibration monitor in dependence on one, other or both of a vibration level value as determined in dependence on sensed vibration and a predetermined vibration value. Alternatively or in addition the vibration monitor may comprise at least one of: an actuator operable to provide an audible output, such as a buzzer; and an actuator operable to provide an output susceptible to pallesthesia, such as a vibrating motor. The processor may be operative to actuate such an actuator in dependence on a vibration exposure determined in dependence on one, other or both of sensed vibration and a predetermined vibration value. For example an actuator may be actuated when a daily vibration exposure limit is reached.

According to a second aspect of the present invention there is provided a vibration monitoring arrangement comprising a vibration monitor according to the first aspect of the present invention. The vibration monitoring arrangement may further comprise a tool arrangement.

The tool arrangement may be configured to be attached to a power tool. The tool arrangement may be configured to store power tool data and more specifically power tool data for the power tool to which the tool arrangement is to be attached or is attached. The vibration monitor and the tool arrangement may be configured for transfer of the power tool data from the tool arrangement to the vibration monitor. The vibration monitor and the tool arrangement may be configured for wireless transfer of the power tool data. The tool arrangement may comprise an RFID tag and the vibration monitor may comprise an RFID reader whereby the power tool data may be transferred to the vibration monitor from the tool arrangement. The tool arrangement may be configured to be attached to a power tool by way of adhesive or the like.

The power tool data may comprise at least one of: power tool identification data; a predetermined vibration value; and at least one threshold value. The threshold value may be one of an amplitude threshold value and a frequency threshold value.

Further embodiments of the second aspect of the present invention may comprise one or more features of the first aspect of the present invention.

According to a third aspect of the present invention there is provided a method of monitoring vibration sustained by an operator during use of a power tool, the method comprising:
  sensing vibration sustained by the operator by way of a vibration sensor comprised in a vibration monitor worn by an operator;
  receiving sensed vibration data from the vibration sensor in a processor; and
transforming the received vibration data in the processor whereby the transformed data is more representative than the received vibration data of vibration at a location on a power tool or a workpiece with which the operator is in contact during use of the power tool.

The method may further comprise determining a first frequency spectrum for received vibration data. The frequency spectrum may be determined by way of vibration monitoring apparatus other than the vibration sensor. The frequency spectrum may be determined during a calibration phase or the like. The method may yet further comprise determining a second frequency spectrum for vibration measured on the location on the power tool with which the operator is in contact during use of the power tool. The method may comprise determining a transformation in dependence on the first and second frequency spectra.

According to a further aspect of the present invention there is provided a vibration monitor which is configured to be worn by an operator, the vibration monitor comprising: a vibration sensor operative to sense vibration sustained by the operator; and a processor configured to receive sensed vibration data from the vibration sensor and to transform received vibration data. Embodiments of the further aspect of the present invention may comprise one or more features of the first or second aspect of the present invention.

BRIEF DESCRIPTION OF DRAWINGS

Further features and advantages of the present invention will become apparent from the following specific description, which is given by way of example only and with reference to the accompanying drawings, in which.

DESCRIPTION OF EMBODIMENTS

A vibration monitor 10 according to an embodiment of the present invention is shown in situ on the wrist of a power tool operator. The vibration monitor 10 comprises a housing 12 having the general form of rectangular cuboid and a strap 14 attached to the housing whereby the vibration monitor 10 may be attached to the wrist of the operator in the manner of a wrist watch. A face of the housing 12 defines a rectangular window 16 through which an LCD display may be seen by the operator. An embodiment of the vibration monitor 10 of FIG. 1 comprises a user operable on-off switch whereby the vibration monitor may be turned off to stop recording vibration at inappropriate times, such as when the operator is driving.

Figure 2:
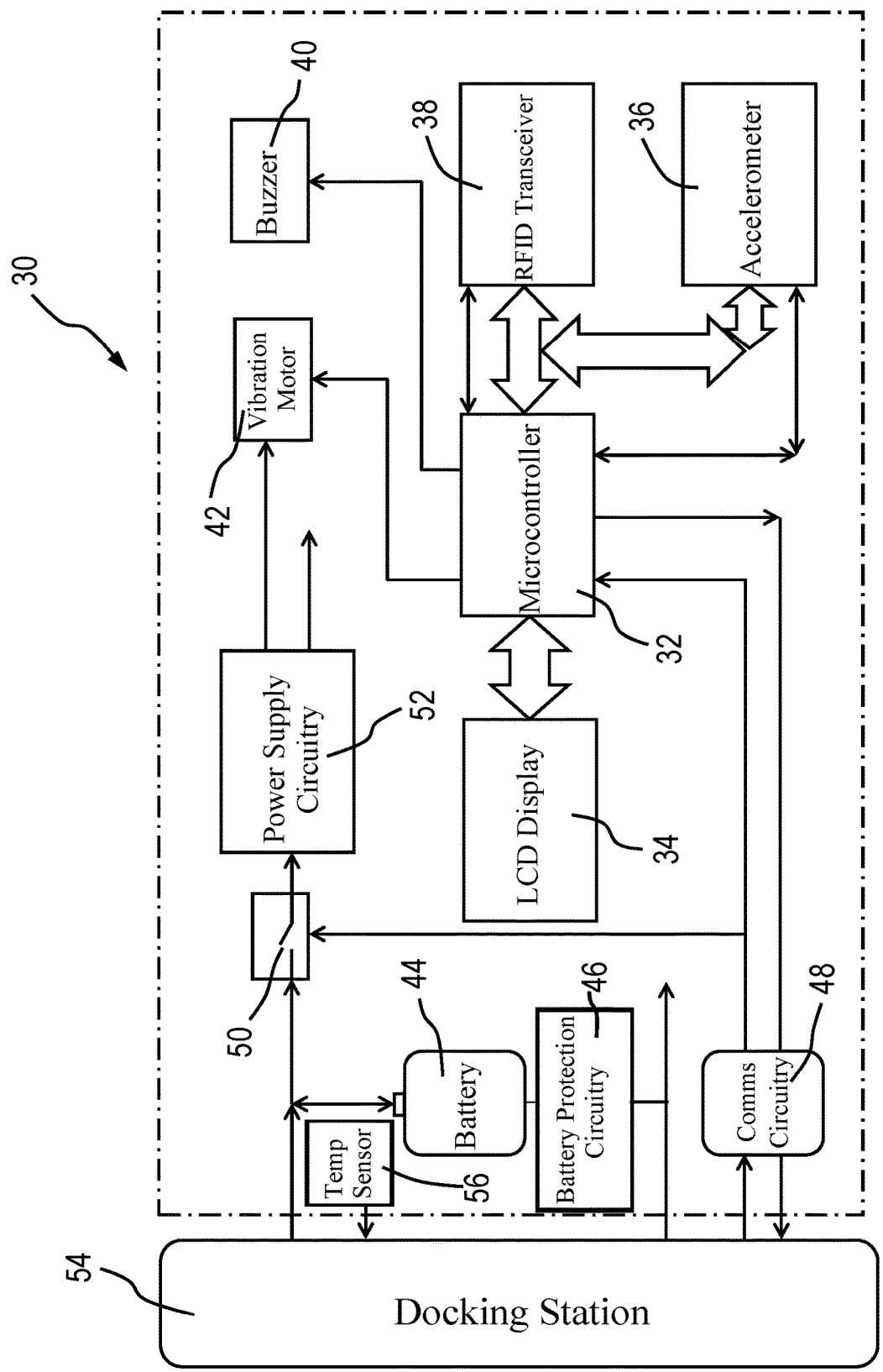
FIG. 2 is a block diagram representation of the embodiment of FIG. 1.

The vibration monitor 30 is represented in block diagram form in FIG. 2. The vibration monitor 30 comprises a microcontroller 32, namely an Atmel ARM Cortex M4 SAM4LS with 512K of flash memory, an LCD 34, which is driven by the microcontroller 32 by way of a i2c bus, an accelerometer 36 (which constitutes a vibration sensor), namely an ST Microelectronics MEMS LIS3DSHTR, and an RFID transceiver 38, namely an NXP 13.56 MHz CLRC66301HN/TR having multiple protocol support. Each of the accelerometer 36 and the RFID transceiver 38 communicates with the microcontroller 32 by way of an SPI bus. The accelerometer 36 comprises an analogue to digital converter. The design of the vibration monitor 30 in respect of the microcontroller 32, the LCD 34, the accelerometer 36 and the RFID transceiver 38 is within the ordinary design capabilities of the person skilled in the art. The vibration monitor 30 further comprises a buzzer 40 and a vibration motor 42 which are operative under control from the microcontroller 32 to provide a warning of different sensory form when vibration exposure exceeds a predetermined level. The design of the vibration monitor 30 in respect of the buzzer 40 and the vibration motor 42 is within the ordinary design capabilities of the person skilled in the art.

The vibration monitor 30 yet further comprises a rechargeable battery 44, battery protection circuitry 46, galvanically isolated communications circuitry 48, an on-off switch 50, power supply circuitry 52 and a temperature sensor 56. The design of the vibration monitor 30 in respect of these components is within the ordinary design capabilities of the person skilled in the art. A docking station 54 is represented in FIG. 2. The docking station 54 is configured to hold plural vibration monitors 30 in respective bays formed in the docking station 54. When received in the docking station 54 the rechargeable battery 44 of the vibration monitor 30 is charged by way of a copper connection between the docking station 54 and the vibration monitor 30. The communications circuitry 48 of the vibration monitor 30 provides for communication of data between the vibration monitor 30 and the docking station 54. Data communicated to the docking station 54 includes the like of vibration exposure data, operator exposure data and Power Spectral Density (PSD) data stored in the vibration monitor 30 during use thereof. Such data is stored for compliance and record keeping purposes and further analysis of power tool usage if such is required. Data communicated to the vibration monitor 30 includes the like of vibration exposure thresholds and other configuration data for the vibration monitor 30 and provides for clearing of data memory within the vibration monitor 30 such as data memory used to store vibration exposure data, operator exposure data and PSD data. The power supply circuitry 52 comprises a regulator and a DC/DC converter which are operative to draw current from the rechargeable battery 44 and provide electrical power of appropriate voltage to each of the buzzer 40 and the vibration motor 42. The on-off switch 50 enables the operator to turn the vibration monitor 30 on and off. The temperature sensor 56 is operative to sense the temperature of the rechargeable battery 44 during charging and to convey the sensed temperature to the docking station 54. Damage to the rechargeable battery 44 may occur if the temperature of the rechargeable battery 44 rises above a threshold temperature. The docking station 54 is therefore configured to cease charging of the rechargeable battery 44 if the sensed temperature rises above a threshold temperature.

Figure 1:
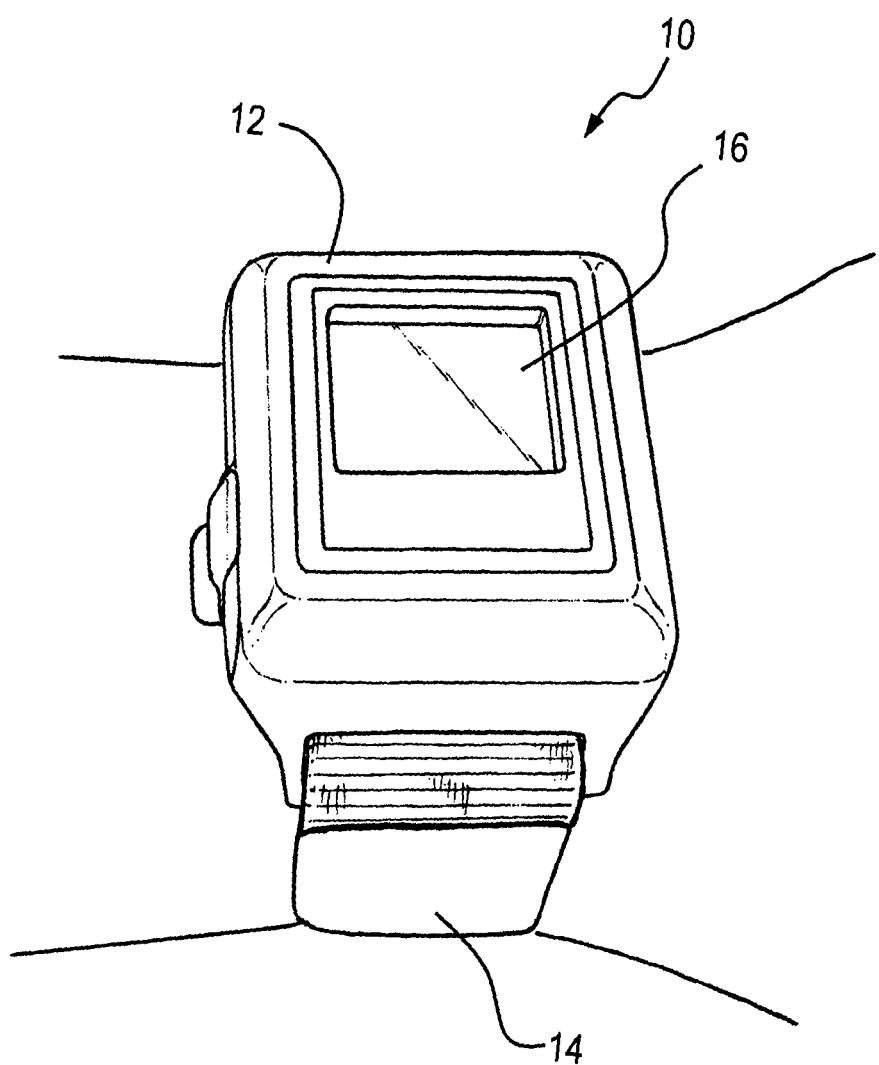
FIG. 1 shows a vibration monitor according to an embodiment of the present invention in situ.

A vibration monitoring arrangement according to a first embodiment of the present invention comprises the vibration monitor 30 of FIGS. 1 and 2 and an RFID tag (not shown). Power tool data is stored in the RFID tag and the RFID tag is brought into use by being attached by way of adhesive to a power tool. The power tool data stored in the RFID tag is described below. A vibration monitoring arrangement according to a second embodiment of the present invention comprises the vibration monitor 30 of FIGS. 1 and 2 with the RFID tag being optional although usually preferred.

Figure 3A:
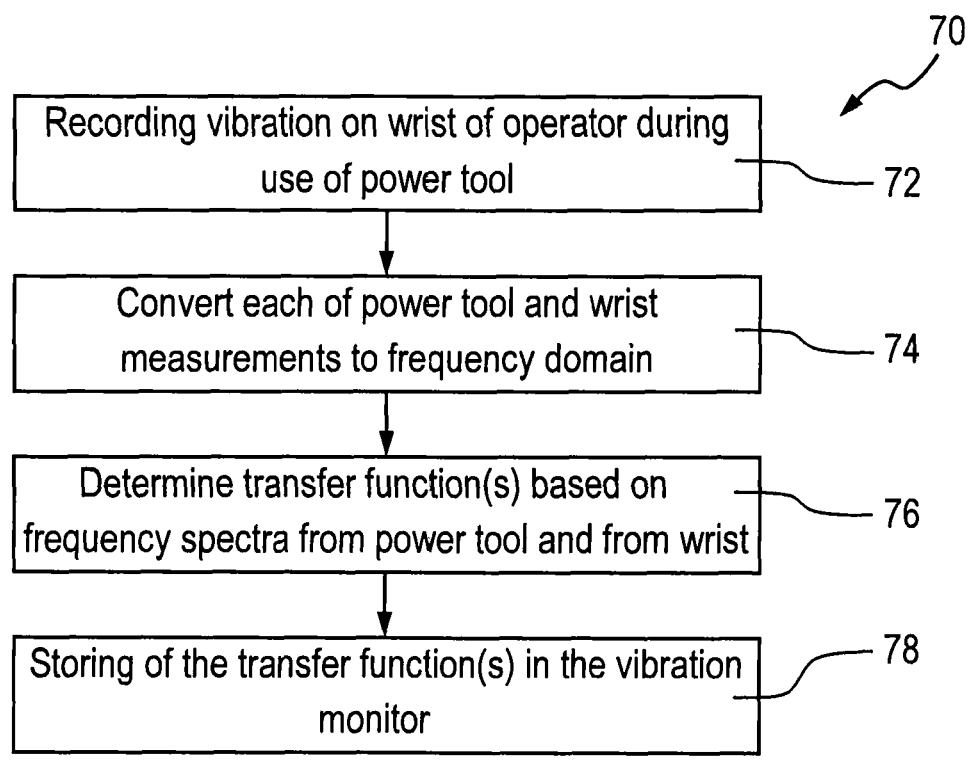
FIG. 3A is a flow chart setting out the main steps during configuration of the vibration monitor of FIG. 1.
Figure 3B:
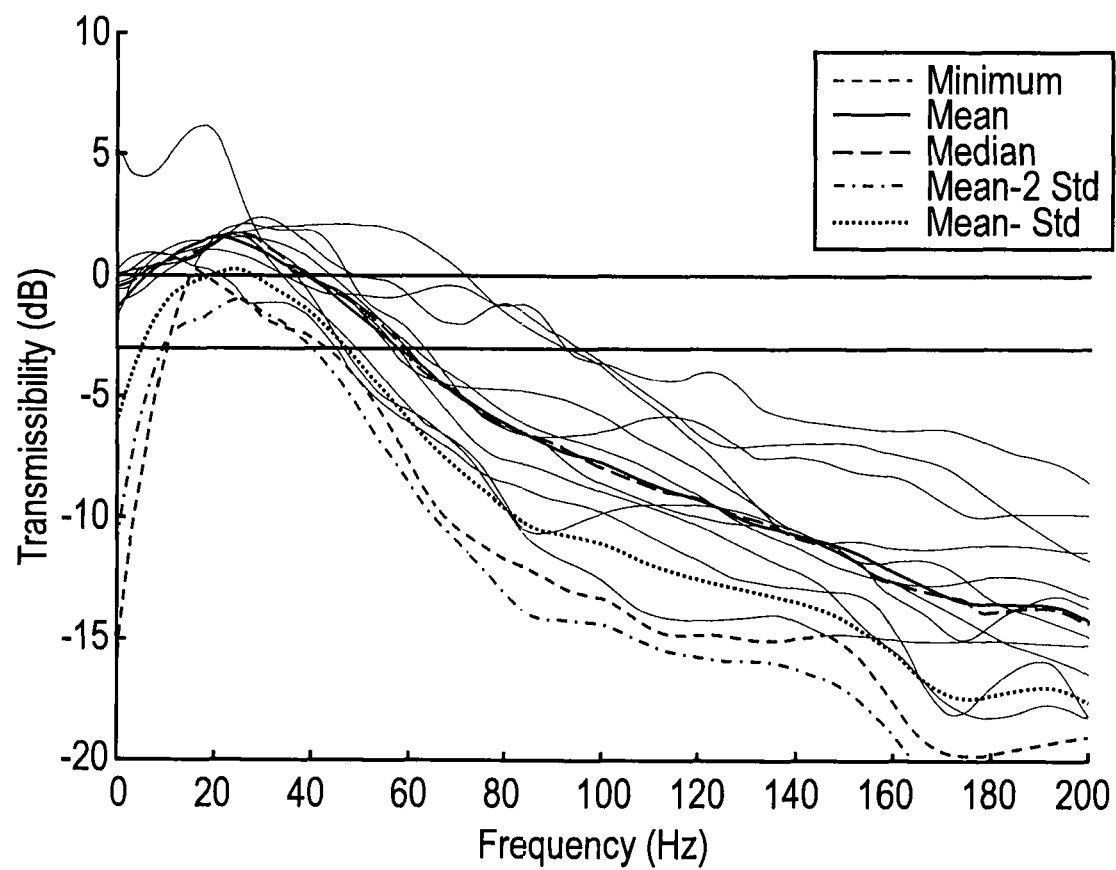
FIG. 3B shows transmissibility against frequency for various data sets.
Figure 3C:
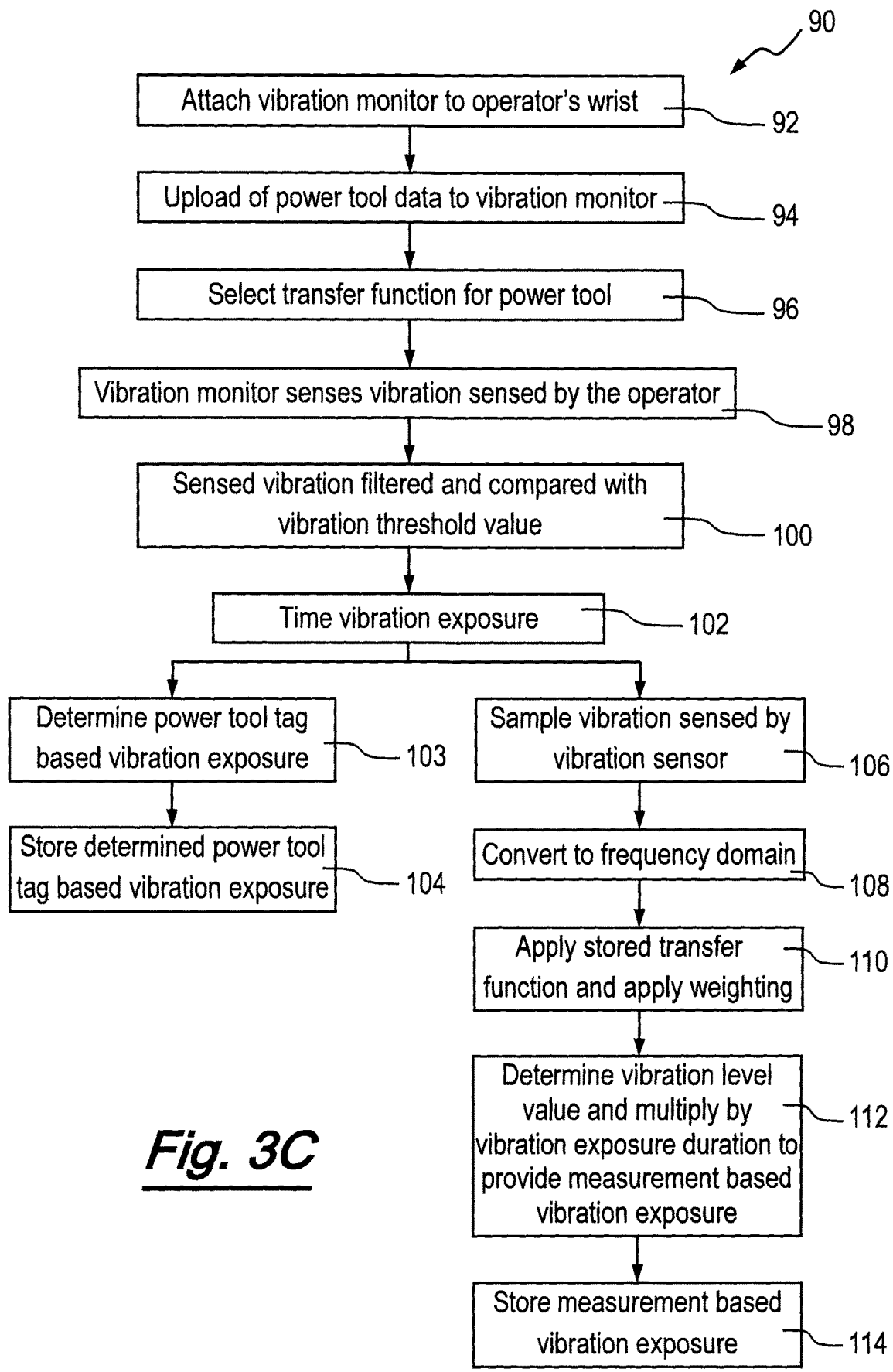
FIG. 3C is a flow chart setting out the main steps during operation of the vibration monitor of FIG. 1.
Figure 4A:
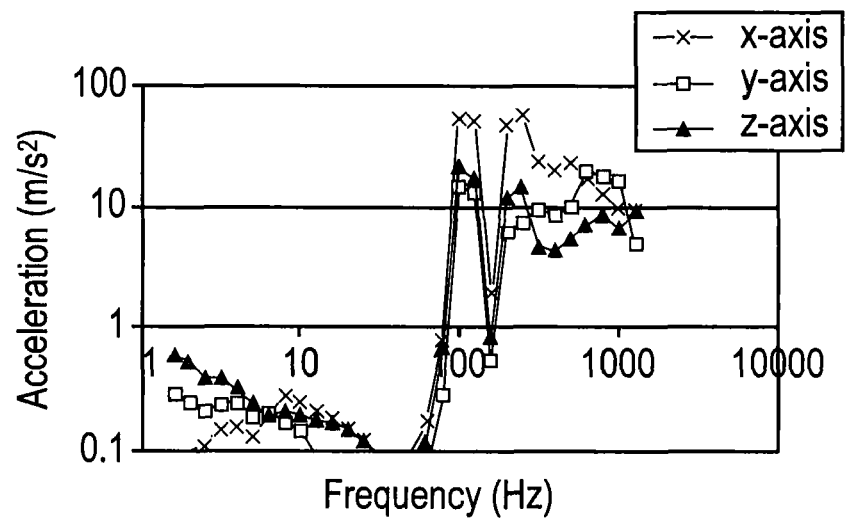
FIG. 4A shows vibration measurements on the wrist during use of a sanding tool.
Figure 4B:
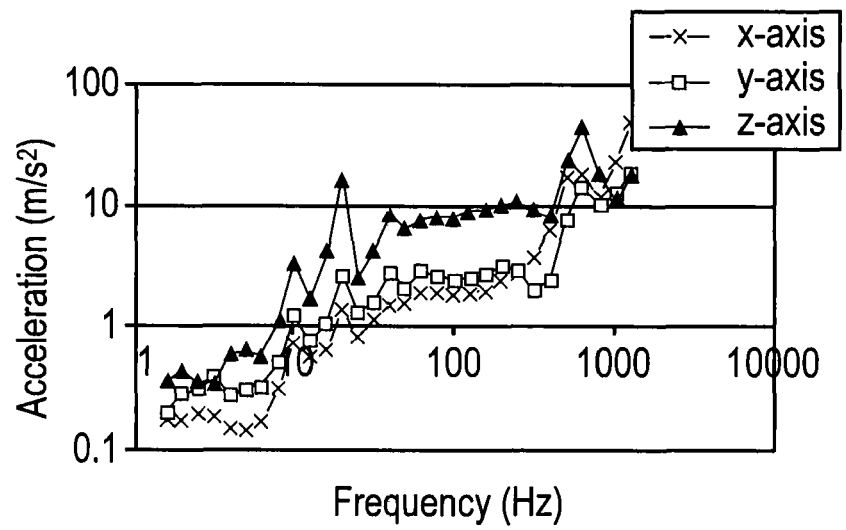
FIG. 4B shows vibration measurements on the wrist during use of a concrete breaking tool.

Configuration and operation of the vibration monitor 30 of FIG. 2 according to the first embodiment will now be described with reference to the flow charts of FIGS. 3A and 3C and the charts shown in FIGS. 3B, 4A and 4B.

Vibration monitoring apparatus (not shown) comprising a vibration sensor other than the vibration sensor comprised in the vibration monitor 30 is used during a configuration phase. The vibration monitoring apparatus is of known form and function and has the capability to sample vibration at a rate at least as high as the vibration monitor 30 and to record the sampled vibration for display and analysis. The vibration sensor of the vibration monitoring apparatus is attached to the power tool under calibration at a location where the power tool is held by an operator and the vibration monitoring apparatus is operative to sample and record vibration of the power tool during use. A weighted frequency average vibration (WFAV) is determined on the basis of the recorded vibration data in accordance with known UK HSE procedure and more specifically as set out in ISO 5349-1 & 2. WFAV is determined on the basis of the root mean square value for vibration in each of the x, y and z axes in accordance with:

$$a_{hwn} = \sqrt{\sum_i (W_{hi} a_{hin})^2}$$

where $a_{hwn}$ is the root mean square acceleration for axis of vibration n, n being one of the x, y and z axes, $W_{hi}$ is the weighting factor for i th one-third-octave band as shown in Table A.2 of ISO 5349-1 and $a_{hin}$ is the root mean square acceleration for axis of vibration n, n being one of the x, y and z axes measured in the i th one-third-octave band in metres per second squared. Thereafter vibration data for the three axes are combined by summing the square of vibration data in each of the three axes and taking the square root of the sum in accordance with:

$$a_{hv} = \sqrt{a_{hwx}^2 + a_{hwy}^2 + a_{hwy}^2}$$

where $a_{hv}$ is the combined value for the three axes and $a_{hwx}$, $a_{hwy}$ and $a_{hwy}$ are the root mean square values for the x, y and z axes respectively as determined in accordance with the equation above. Application of the weighting factor $W_{hi}$ amounts to the application of the band limiting and frequency weighting filters specified in A.1 of ISO 5349-1.

The thus determined combined value is the WFAV (which constitutes a predetermined vibration value). The RFID tag is programmed with the WFAV such that the power tool data comprises the WFAV. The RFID tag is also programmed with an identification code for the power tool and vibration threshold values for the power tool whereby the power tool data comprises the identification code and the vibration threshold values. The RFID tag is further programmed with a noise rating for and a weight of the power tool. The noise rating provides for determination of exposure of the operator to noise based on length of time of use of the power tool. The weight of the power tool also provides a basis for determining physical stress of the user on account of bearing the weight of the power tool during use.

Further configuration in accordance with the present invention will now be described with reference to the flow chart 70 of FIG. 3A which shows the main steps during such further configuration. Further configuration comprises monitoring and recording vibration on the wrist of the operator during use of the power tool 72. Monitoring of vibration on the wrist of the operator is accomplished by a second vibration sensor comprised in the vibration monitoring apparatus which is attached to the wrist such that the vibration monitoring apparatus is operative to sample and record vibration of the wrist at the same time as vibration of the power tool during use of the power tool. The measurements on the power tool and on the wrist are converted to the frequency domain by way of Welch's method 74. The root mean square (RMS) amplitude is then determined for each frequency band for the x, y and z axes and summed as the root of the squares. Hence the total RMS values at the power tool and at the wrist are determined. A transfer function of transmissibility as a function of frequency is determined by dividing the RMS value at the wrist by the RMS value at the source 76. In one form, the above approach is performed for plural different operators whereby a transfer function for an average operator is obtained. In another form, the above approach performed for a particular operator whereby a transfer function for a particular operator is obtained. In yet another form, plural transfer functions are obtained in respect of plural different tools. FIG. 3B shows transmissibility for eleven data sets acquired with a shaker rather than a power tool; nevertheless the traces in FIG. 3B demonstrate the principle followed in respect of power tools. Aside from curves for the eleven data sets, FIG. 3B shows the minimum, the mean, the median, the mean minus the standard deviation and the mean minus 2 standard deviation. Here, the mean minus the standard deviation was selected as providing the most appropriate transfer function. At least one transfer function is then stored in the vibration monitor 78.

Operation of the vibration monitor of FIGS. 1 and 2 will now be described with reference to the flow chart 90 shown in FIG. 3C. The operator attaches the vibration monitor 30 to his wrist and switches on the vibration monitor 92. When the operator takes hold of a power tool the RFID communication link between the vibration monitor 30 and the RFID tag on the tool is operative to provide for upload of the power tool data 94. Alternatively the operator works with a fixed power tool, such as a grinder, and holds a workpiece with which the power tool is brought into contact whereby vibration of the power tool is coupled to the operator by way of the workpiece. As described above the power tool data comprises the WFAV, an identification code for the power tool and vibration threshold values for the power tool. Where the vibration monitor stores plural transfer functions, microcontroller 32 is operative to select one of the plural transfer functions in dependence on the identification code for the power tool 96.

The accelerometer 36 comprised in the vibration monitor is then operative to sense vibration sustained by the operator during use of the power tool 98. The sensed vibration is sampled by the analogue to digital converter comprised in the microcontroller 32 every one second for 320 ms at a rate of 1.6 kHz. The sampled vibration data is filtered with a high pass digital filter and a notch digital filter to remove vibration data from sources other than a power tool 100, e.g. vibration from the operator waving or sustained by the operator from the floor through his legs. The microcontroller 32 is further configured to analyse a frequency spectrum of the sampled vibration data and to determine at least one dominant frequency. The power tool is categorized on the basis of dominant frequency determination and one of a low pass and a high pass filter applied to the sampled vibration data 100. By way of example FIG. 4A shows vibration traces recorded on a sanding tool. By way of further example FIG. 4B shows vibration traces recorded on a concrete breaking tool. The traces in FIG. 4A show a steep increase in vibration amplitude from about 100 Hz upwards. The traces in FIG. 4B show a spike in vibration amplitude at 16 Hz to 20 Hz. The high pass filter is appropriate for the sanding tool and a low pass filter is appropriate for the concrete breaking tool.

As the sensed vibration is sampled and stored it is compared with the vibration threshold value for the power tool 100. More specifically the amplitude of the sampled vibration is compared with a vibration amplitude threshold of 3.0 m/s$^2$. If the sampled vibration exceeds the vibration threshold value, the microcontroller 32 is operative to start timing vibration exposure 102. When the sampled vibration fails to exceed the vibration threshold value, timing of vibration exposure stops.

Measuring vibration exposure comprises two parallel vibration exposure processes. The vibration exposure duration as determined by the timing process described above is used in each of the two parallel vibration exposure processes.

A first vibration exposure process is based on the WFAV uploaded from the RFID tag. The first vibration exposure process comprises multiplying the vibration exposure duration by the square of the WFAV and by the constant 2 to determine a power tool tag based vibration exposure 103. The power tool tag based vibration exposure is stored and added to power tool tag based vibration exposure previously determined during the operator's shift of work 104.

A second vibration exposure process is based on vibration sensed by the tri-axial accelerometer 36 which is sampled by the analogue to digital converter of the microcontroller 32 every one second for 320 ms at a rate of 1.6 kHz 106. The time domain samples are converted to the frequency domain by way of Welch's method with a large time window of, for example, 10 seconds to provide a high frequency resolution 108. The RMS amplitude in each frequency band of each of the x, y and z frequency domain vibration data is transformed using the stored transfer function and then weighted in accordance with ISO 5349-1 110. Thereafter the RMS amplitudes in each of the x, y and z axes are summed over all the frequency bands and combined for the three axes 110 by summing the square of RMS vibration data in each of the three axes and taking the square root of the sum. The thus determined combined value is the vibration level value 112. A measurement based vibration exposure is provided by multiplying the square of the vibration level value by the vibration exposure duration 112. The measurement based vibration exposure is stored and added to measurement based vibration exposure previously determined during the operator's shift of work 114.

If the microcontroller 32 determines that one of the accumulated power tool tag based vibration exposure and the accumulated measurement based vibration exposure exceeds the vibration exposure threshold stored in the vibration monitor, the microcontroller 32 is operative to actuate the buzzer 40 and the vibration motor 42 to provide a warning to the operator. The microcontroller 32 is further operative to display at least one of the accumulated power tool tag based vibration exposure and the accumulated measurement based vibration exposure to the operator by way of the LCD display 34.

Further to the two vibration exposure processes described above, the microcontroller 32 is operative to determine a Power Spectral Density (PSD) from the sampled vibration data and to store the PSD in memory. The PSD is determined on the basis of frequency increments of 3.125 Hz between 3 Hz and 200 Hz. The energy received at the wrist of the operator on account of vibration is determined by integration of the PSD to thereby provide an energy value. The microcontroller 32 is further operative to determine an operator exposure value in dependence on the energy value, the tool tag based vibration exposure and the measurement based vibration exposure and also the duration of use of the power tool and the tool type. The operator exposure value (OEV) is formed in accordance with:

$$OEV = K_1 D + K_2 T + K_3 L + K_4 P + K_5 E$$

where D is duration of use, T is tool type, L is the tool tag based vibration exposure, P is the measurement based vibration exposure, E is the energy value and the constants, $K_1$ to $K_5$, are set during calibration to provide appropriate weighting of the various factors and may be any number including zero. The constants, $K_1$ to $K_5$, are determined on the basis of previous measurements and reflect relative contribution of the various factors which reflect risk to the operator.

At the end of the operator's shift, the operator removes the vibration monitor 30 from his wrist and places it in a bay in the docking station 54 whereupon recharging of the rechargeable battery comprised in the vibration monitor commences. In addition the accumulated tool tag based vibration exposure, the accumulated measurement based vibration exposure and power spectral density data are wirelessly conveyed to the docking station 54 along with the operator exposure value. When stored in the docking station 54 the accumulated tool tag based vibration exposure, the accumulated measurement based vibration exposure and the power spectral density data are available for subsequent review and analysis on the like of a Personal Computer which receives data stored by the presently described vibration monitor 30 and other vibration monitors of the same form and function by way of a communications port of known form and function comprised in the docking station 54.

Figure 5:
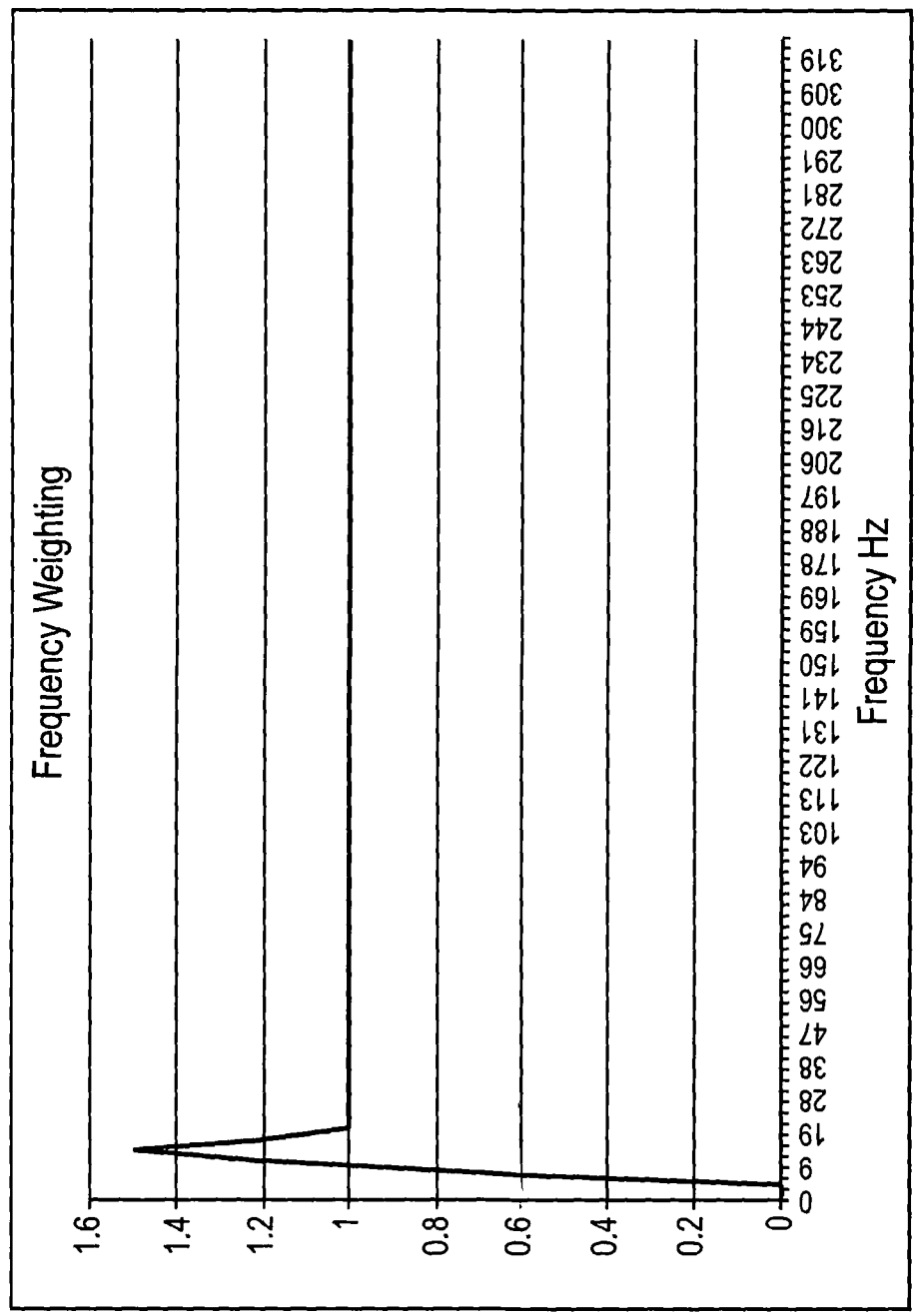
FIG. 5 is a graphical representation of a transfer function used in a second embodiment of the present invention.

Configuration and operation of the vibration monitor 30 of FIG. 2 according to the second embodiment will now be described. There is no requirement for a calibration phase for each power tool or each class of power tools according to the first embodiment and as represented in FIG. 3A. Instead the same transfer function is used for each different power tool or each different class of power tools. The transfer function is represented in FIG. 5. Considering the graph shown FIG. 5, the weighting applied by the transfer function below 6 Hz corresponds to the weighting specified in Table A.2, Annex A EN ISO 5349:2001. In the frequency range of 6 Hz to 16 Hz the transfer function is operative to amplify the sensed vibration as shown in FIG. 5. Above 16 Hz the transfer function is operative to neither amplify nor attenuate the sensed vibration as shown in FIG. 5.

Operation of the vibration monitor 30 of FIG. 2 according to the second embodiment will now be described further. The operator attaches the vibration monitor 30 to his wrist and switches on the vibration monitor 92 as described above in respect of the first embodiment. In contrast with the first embodiment, there is no need to upload data from an RFID tag attached to the power tool because the vibration monitor is capable of making and recording vibration measurements without such uploaded data. The vibration monitor is therefore operative in the absence of an RFID tag attached to the power tool in use. However much of the further functionality associated with data stored in the RFID tag would be lost, such as associating recorded data with particular power tools, and therefore more usually but not exclusively the vibration monitor is operative in cooperation with an RFID tag. When the operator sustains vibration from the power tool or from a workpiece which is caused to vibrate by the power tool, the vibration monitor is operative to acquire and store vibration data as described above with reference to the first embodiment. Processing of the acquired vibration data according to the second embodiment will now be described.

The processor is operative to combine acceleration measured in each of the x, y and z axes in accordance with the following equation to provide a single vector sum, $a_v(t)$:

$$a_v(t) = \sqrt{[K_x a_x(t)]^2 + [K_y a_y(t)]^2 + [K_z a_z(t)]^2}$$

where $K_x$, $K_y$ and $K_z$ are weighting factors. The processor is then operative to determine the Fourier transform, $a_v(f)$, of $a_v(t)$. Thereafter the processor is operative to calculate the r.m.s weighted acceleration, $a_{hw}$, in accordance with equation A.1 Annex A of EN ISO 5349-1:2001, i.e.

$$a_{hw} = \sqrt{\sum_i (W_{hi} a_{hi})^2}$$

where $W_{hi}$ is the weighting factor for the i th one-third-octave band as shown in FIG. 5 and described further above.

Otherwise operation according to the second embodiment is in accordance with operation according to the first embodiment as described above.

In forms of the invention, the vibration monitor 30 is operative selectively in accordance with one or other of the first and second embodiments or in accordance with both embodiments. Selective operation is by way of manual operation of controls of the vibration monitor prior to use or by software control of the vibration monitor during a configuration phase.

The invention claimed is:

1. A vibration monitor releasably attached to an arm or hand of an operator during use of a power tool, the vibration monitor comprising:
 a vibration sensor sensing vibration sustained by the arm or hand of the operator when the vibration monitor is attached to the arm or hand of the operator; and
 a processor receiving sensed vibration data from the vibration sensor and applying a transformation to the received sensed vibration data to provide transformed data whereby the transformed data is more representative than the received sensed vibration data of vibration at a location on a power tool or a workpiece with which the operator is in contact during use of the power tool,
 wherein the processor determines vibration exposure risk for the operator during use of the power tool, the vibration exposure risk determined in dependence on the transformed data, and
 wherein the transformation is obtained by a calibration process comprising: making a first vibration measurement at the location on a power tool or a workpiece with which an operator is in contact during use of the power tool; making a second vibration measurement at the location of the vibration monitor where the vibration monitor is attached to the operator; and deriving the transformation from the first and second vibration measurements.

2. The vibration monitor according to claim 1 in which the transformation amplifies the received sensed vibration data in a predetermined range of frequencies to thereby address attenuation by the body of the operator of vibration sustained by the operator at the location of contact of the operator with the power tool or the workpiece.

3. The vibration monitor according to claim 2 in which the predetermined range of frequencies is between 6 Hz and 16 Hz.

4. The vibration monitor according to claim 2 in which the transformation neither amplifies nor attenuates the received sensed vibration data above the predetermined range of frequencies.

5. The vibration monitor according to claim 2 in which the transformation attenuates the received sensed vibration data below the predetermined range of frequencies.

6. The vibration monitor according to claim 5 in which the transformation completely attenuates the received sensed vibration data below the predetermined range of frequencies.

7. The vibration monitor according to claim 1 in which the transformation attenuates the received sensed vibration data in a low frequency range, amplifies the received sensed vibration data in a medium frequency range and neither amplifies nor attenuates the received sensed vibration data in a high frequency range.

8. The vibration monitor according to claim 1 in which the transformation is configured selectively for one of plural classes of power tool, a data store comprised in the vibration monitor storing plural different transformations, each transformation being for a different one of: class of power tool; and particular power tool.

9. The vibration monitor according to claim 1 in which the transformation is applied irrespective of a vibration characteristic of the power tool with which the vibration monitor is used whereby a same transformation is used with different power tools.

10. The vibration monitor according to claim 1 in which the processor transforms time domain sensed vibration data received from the vibration sensor to frequency domain vibration data.

11. The vibration monitor according to claim 10 in which the processor determines a Power Spectral Density (PSD) in dependence on the frequency domain vibration data; and determines an energy value by integration over a predetermined interval of the PSD.

12. The vibration monitor according to claim 10 in which the processor determines a root mean square value of frequency domain vibration data after application of the transformation to provide more representative data.

13. The vibration monitor according to claim 12 in which the processor determines the root mean square value in accordance with:

$$a_{hw} = \sqrt{\sum_i (W_{hi} a_{hi})^2}$$

where $a_{hw}$ is the root mean square acceleration, $W_{hi}$ is a weighting factor for the i th one-third-octave band applied by way of the transformation, and an' is the acceleration measured in the i th one-third-octave band in metres per second squared.

14. The vibration monitor according to claim 1 and where the vibration sensor is a tri-axial vibration sensor, wherein the processor sums sensed vibration data in each of the three axes.

15. The vibration monitor according to claim 14 in which the processor combines sensed vibration data in three axes in accordance with:

$$a_{hv} = \sqrt{a_{hwx}^2 + a_{hwy}^2 + a_{hwy}^2}$$

where $a_{hv}$ is a vibration level value and $a_{hwx}$, $a_{hwy}$ and $a_{hwy}$ are root mean square values for the x, y and z axes respectively.

16. The vibration monitor according to claim 14 in which the processor combines sensed vibration data in three axes, x, y and z, in accordance with:

$$a_v(t) = \sqrt{[K_x a_x(t)]^2 + [K_y a_y(t)]^2 + [K_z a_z(t)]^2}$$

where $K_x$, $K_y$ and $K_z$ are weighting factors.

17. The vibration monitor according to claim 1 wherein obtaining the transformation comprises: converting the first and second vibration measurements to the frequency domain to obtain first and second frequency spectra respectively; and deriving the transformation from the first and second frequency spectra.

18. The vibration monitor according to claim 1 wherein the calibration process is performed in respect of plural different operators and further comprises deriving the transformation for an average operator based on vibration measurements made in respect of the plural different operators.

19. The vibration monitor according to claim 1 wherein the transformation amplifies the received sensed vibration data by a factor of at least 1.1 in a frequency range between 6 Hz and 20 Hz.

20. The vibration monitor according to claim 19 wherein the transformation amplifies the received sensed vibration data by a factor of no more than 1.6 in the frequency range between 6 Hz and 20 Hz.

21. A method of monitoring vibration sustained by an operator during use of a power tool, the method comprising:
sensing vibration sustained by an arm or hand of the operator by way of a vibration sensor comprised in a vibration monitor releasably attached to the arm or hand of the operator;
receiving sensed vibration data from the vibration sensor in a processor;
applying in the processor a transformation to the received sensed vibration data to provide transformed data whereby the transformed data is more representative than the received sensed vibration data of vibration at a location on a power tool or a workpiece with which the operator is in contact during use of the power tool; and
determining in the processor vibration exposure risk for the operator during use of the power tool, vibration exposure risk determined in dependence on the transformed data,
wherein the transformation is obtained by a calibration process comprising: making a first vibration measurement at the location on a power tool or a workpiece with which an operator is in contact during use of the power tool; making a second vibration measurement at the location of the vibration monitor where the vibration monitor is attached to the operator; and deriving the transformation from the first and second vibration measurements.

* * * * *